US008831713B2

(12) United States Patent
Stadler et al.

(10) Patent No.: US 8,831,713 B2
(45) Date of Patent: Sep. 9, 2014

(54) PREVENTION OF FALSE ASYSTOLE OR BRADYCARDIA DETECTION

(75) Inventors: Robert W. Stadler, Shoreview, MN (US); Tim Dirk Jan Jongen, Heerlen (NL); Richard PM Houben, Lanaken (BE)

(73) Assignee: Medtronic, Inc., Minneapolis, MN (US)

( * ) Notice: Subject to any disclaimer, the term of this patent is extended or adjusted under 35 U.S.C. 154(b) by 1045 days.

(21) Appl. No.: 12/846,224

(22) Filed: Jul. 29, 2010

(65) Prior Publication Data
US 2012/0029373 A1 Feb. 2, 2012

(51) Int. Cl.
  *A61B 5/04* (2006.01)
  *A61N 1/37* (2006.01)
  *A61B 5/0456* (2006.01)

(52) U.S. Cl.
  CPC ............... *A61N 1/37* (2013.01); *A61B 5/0456* (2013.01)
  USPC ............................ 600/513; 600/516; 600/521

(58) Field of Classification Search
  USPC ......................... 600/513, 516, 521
  See application file for complete search history.

(56) References Cited

U.S. PATENT DOCUMENTS

| 5,117,824 | A | 6/1992 | Keimel et al. |
| 5,545,186 | A | 8/1996 | Olson et al. |
| 5,755,736 | A | 5/1998 | Gillberg et al. |
| 6,304,773 | B1 | 10/2001 | Taylor et al. |
| 6,694,187 | B1 | 2/2004 | Freeman |
| 7,027,858 | B2 | 4/2006 | Cao et al. |
| 7,392,081 | B2 | 6/2008 | Wagner et al. |
| 7,756,570 | B1 | 7/2010 | Bornzin |
| 7,761,150 | B2 | 7/2010 | Ghanem et al. |
| 2003/0060723 | A1 | 3/2003 | Joo et al. |
| 2004/0039419 | A1 | 2/2004 | Stickney et al. |
| 2004/0039420 | A1* | 2/2004 | Jayne et al. ................. 607/5 |
| 2004/0049120 | A1* | 3/2004 | Cao et al. ................. 600/521 |
| 2004/0215239 | A1 | 10/2004 | Favet et al. |
| 2004/0215258 | A1 | 10/2004 | Lovett et al. |
| 2007/0038253 | A1 | 2/2007 | Kim et al. |
| 2009/0187227 | A1 | 7/2009 | Palreddy et al. |
| 2010/0114199 | A1 | 5/2010 | Krause et al. |

OTHER PUBLICATIONS

International Preliminary Report on Patentability from corresponding PCT Application Serial No. PCT/US2011/033560 dated Feb. 7, 2013 (8 pages).
International Search Report and Written Opinion of international application No. PCT/US2011/033560, dated Jul. 5, 2011, 13 pp.

* cited by examiner

*Primary Examiner* — Nicole F Lavert
(74) *Attorney, Agent, or Firm* — Michael C. Soldner

(57) ABSTRACT

In general, this disclosure is directed to signal processing based methods to reject undersensing in a signal indicative of cardiac activity, e.g., ECG. The undersensing may be due to very small signal amplitudes or due to a sudden increase in single peak amplitude resulting in an increased sensing threshold. The undersensing may result in falsely detecting a cardiac event, e.g., asystole or bradycardia. The techniques of this disclosure monitor the behavior of the signal to determine when a detected asystole is false.

24 Claims, 9 Drawing Sheets

PREVENTION OF FALSE ASYSTOLE OR BRADYCARDIA DETECTION

TECHNICAL FIELD

The invention relates to medical devices, and, more particularly, to medical devices that sense a signal indicative of cardiac activity.

BACKGROUND

A variety of medical devices for delivering a therapy and/or monitoring a physiological condition have been used clinically or proposed for clinical use in patients. Examples include medical devices that deliver therapy to and/or monitor conditions associated with the heart, muscle, nerve, brain, stomach or other organs or tissues. Some therapies include the delivery of electrical signals, e.g., stimulation, to such organs or tissues. Some medical devices may employ one or more elongated electrical leads carrying electrodes for the delivery of therapeutic electrical signals to such organs or tissues, electrodes for sensing intrinsic electrical signals within the patient, which may be generated by such organs or tissue, and/or other sensors for sensing physiological parameters of a patient. Other medical devices do not include leads, and instead include electrodes and/or sensors formed on or located within a housing of the device.

In systems that include medical leads, the leads may be configured to allow electrodes or other sensors to be positioned at desired locations for delivery of therapeutic electrical signals or sensing. For example, electrodes or sensors may be carried at a distal portion of a lead. A proximal portion of the lead may be coupled to a medical device housing, which may contain circuitry, such as signal generation and/or sensing circuitry. In some cases, the medical leads and the medical device housing are implantable within the patient. In systems that do not include medical leads, electrodes and/or sensors may be located within the medical device housing, which may be positioned at a location that allows delivery of therapeutic electrical signals or sensing of bioelectrical signals. Medical devices with a housing configured for implantation within the patient may be referred to as implantable medical devices.

Implantable cardiac pacemakers or cardioverter-defibrillators, for example, provide therapeutic electrical signals to the heart via electrodes carried by one or more implantable medical leads. The therapeutic electrical signals may include pulses or shocks for pacing, cardioversion, or defibrillation. In some cases, a medical device may sense intrinsic depolarizations of the heart, and control delivery of therapeutic signals to the heart based on the sensed depolarizations. Upon detection of an abnormal rhythm, such as bradycardia, tachycardia or fibrillation, an appropriate therapeutic electrical signal or signals may be delivered to restore or maintain a more normal rhythm. For example, in some cases, an implantable medical device may deliver pacing stimulation to the heart of the patient upon detecting bradycardia or tachycardia, and deliver cardioversion or defibrillation shocks to the heart upon detecting tachycardia or fibrillation.

Another example implantable medical device is an implantable or insertable cardiac monitor, which, in some examples, may not deliver therapy, and may not include leads. An implantable cardiac monitor may include electrodes formed on or integral with its housing for sensing cardiac electrical activity, e.g., intrinsic depolarizations of the heart. An implantable cardiac monitor may include other sensors, e.g., pressure, temperature, motion, or the like, formed on or located within its housing. An implantable cardiac monitor may analyze the cardiac electrical activity to identify cardiac arrhythmias, such as asystole, bradycardia, tachycardia, or fibrillation. An implantable cardiac monitor may store signals representing the cardiac electrical activity, e.g., cardiac electrograms, and any analysis of the signals, for later retrieval by a user.

SUMMARY

In general, the disclosure describes techniques for reducing undersensing of cardiac depolarizations due to, as examples, relatively small electrocardiogram (ECG) signal amplitudes or a relatively high depolarization sensing threshold resulting from a sudden increase in a single R-wave peak amplitude, e.g., due to movement of sensing electrodes. Undersensing of cardiac depolarizations may result in false detection of an asystole or bradycardia. The techniques of this disclosure may reduce undersensing without compromising asystole or bradycardia detection sensitivity.

In one example, the disclosure is directed to a method comprising sensing a signal indicative of cardiac electrical activity, comparing an amplitude of the signal to a first threshold, detecting at least one of a asystole or a bradycardia based on the comparison of the amplitude of the signal to the first threshold, comparing an amplitude of at least one R-wave detected in the signal to at least a second threshold, and determining whether the detection of the asystole or the bradycardia is false based on the comparison of the amplitude of the detected R-wave to the at least second threshold.

In another example, the disclosure is directed to a medical system comprising a sensing module that senses a signal indicative of cardiac electrical activity, a detector module that compares an amplitude of the signal to a first threshold, and detects at least one of a asystole or a bradycardia based on the comparison of the amplitude of the signal to the first threshold, at least a first comparison module that compares an amplitude of at least one R-wave detected in the signal to at least a second threshold, and a processor that determines whether the detection of the asystole or the bradycardia is false based on the comparison of the amplitude of the detected R-wave to the at least second threshold by the at least first comparison module.

In another example, the disclosure is directed to a medical system comprising means for sensing a signal indicative of cardiac electrical activity, means for comparing an amplitude of the signal to a first threshold, means for detecting at least one of a asystole or a bradycardia based on the comparison of the amplitude of the signal to the first threshold, means for comparing an amplitude of at least one R-wave detected in the signal to at least a second threshold, and means for determining whether the detection of the asystole or the bradycardia is false based on the comparison of the amplitude of the detected R-wave to the at least second threshold.

In another example, the disclosure is directed to an article of manufacture comprising a computer-readable medium comprising instructions that, upon execution, cause a processor to sense a signal indicative of cardiac electrical activity, compare an amplitude of the signal to a first threshold, detect at least one of a asystole or a bradycardia based on the comparison of the amplitude of the signal to the first threshold, compare an amplitude of at least one R-wave detected in the signal to at least a second threshold, and determine whether the detection of the asystole or the bradycardia is false based on the comparison of the amplitude of the detected R-wave to the at least second threshold.

In another aspect, the disclosure is directed to an article of manufacture comprising a computer-readable storage medium. The computer-readable storage medium comprises computer-readable instructions for execution by a processor. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein.

The details of one or more examples are set forth in the accompanying drawings and the description below. Other features, objects, and advantages will be apparent from the description and drawings, and from the claims.

DETAILED DESCRIPTION

Figure 1A:
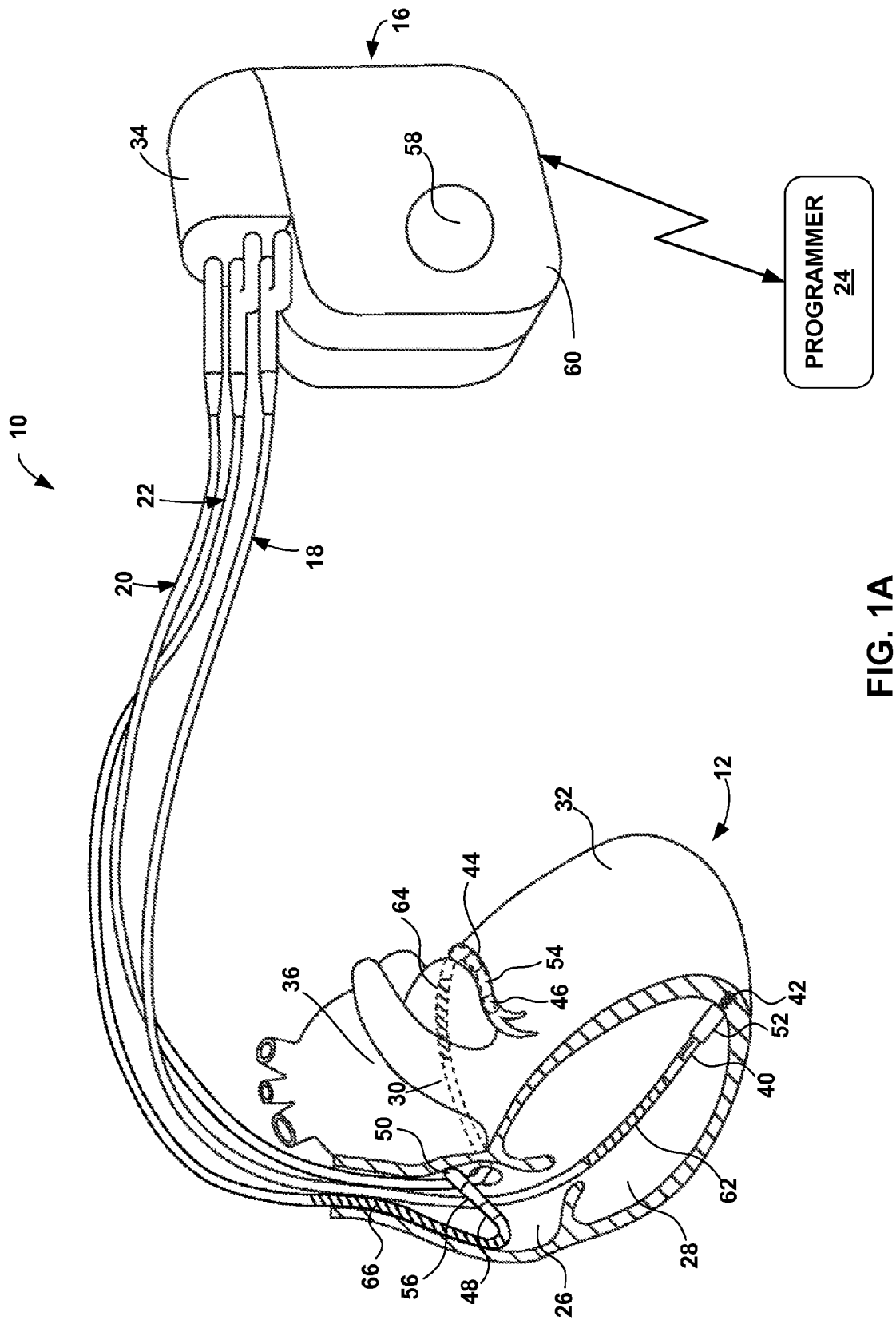
FIGS. 1A-1C illustrate example systems that may be used for sensing of physiological parameters of a patient and/or to provide therapy to a heart of a patient.

A variety of medical devices monitor an electrocardiogram (ECG) of a patient to detect cardiac depolarizations therein. Such medical devices may detect arrhythmias based on the detected depolarizations, such as fibrillation, tachycardia, bradycardia, or asystole. As used herein, an ECG refers to any signal received by a medical device via electrodes that indicates electrical activity, e.g., depolarizations and repolarizations, of a heart.

Failure of a medical device to detect cardiac depolarizations may cause the medical device to falsely detect an asystole or bradycardia. The failure of the medical device to detect cardiac depolarizations may be due to a variety of reasons. Failure to detect cardiac depolarizations typically occurs when peak amplitudes of the ECG associated with the depolarizations are below a sensing threshold. This may be caused by a relatively low average signal amplitude, e.g., due to a sudden drop in signal amplitude as a result of posture shift. In some medical devices, the threshold used to detect peaks in the ECG associated with cardiac depolarizations is adjustable based on the amplitude of one or more previously detected peaks. In such devices, another cause of failure to detect cardiac depolarizations may be a temporarily high threshold due to an unusually large peak amplitude of the ECG for a previous depolarization. The fluctuations in ECG signal amplitude that may cause undersensing of cardiac depolarizations may be, for example, due to shifting of electrodes, which may or may not be located on leads, due to patient posture changes, sources of interference or artifact, such as patient movement artifacts or electromagnetic interference, or cardiac events, such as pre-ventricular contractions (PVCs).

In some cases, a medical device provides information regarding detection of arrhythmias, e.g., asystole and bradycardia, for analysis by a clinician. The clinician may make diagnoses of conditions of a patient and, in some cases, prescribe therapy based on the information. In some cases, a falsely-detected asystole or bradycardia may result in unnecessary delivery of stimulation to a patient by a medical device (e.g., cardiac pacing by a pacemaker). In some cases, a falsely-detected asystole or bradycardia by a medical device may result in inaccurate diagnosis of a patient condition by a clinician who reviews data regarding detection of asystole or bradycardia by the medical device, which in turn may result in unnecessary prescription of a therapy, e.g., pharmaceutical or a device to provide pacing.

In general, this disclosure is directed to signal processing-based techniques to determine occurrence of false detection of asystole or bradycardia without compromising asystole or bradycardia detection sensitivity. The signal processing techniques may provide the ability to detect episodes of low amplitude signals, and disable asystole or bradycardia detection and/or flag those episodes as low confidence. Although the techniques of this disclosure are primarily described with respect to falsely detecting asystole or bradycardia, the techniques described herein may additionally or alternatively apply to detection of other events based on behavior and characteristics of cardiac signals. For illustrative purposes, the techniques of this disclosure will be described with respect to asystole.

Figure 1B:
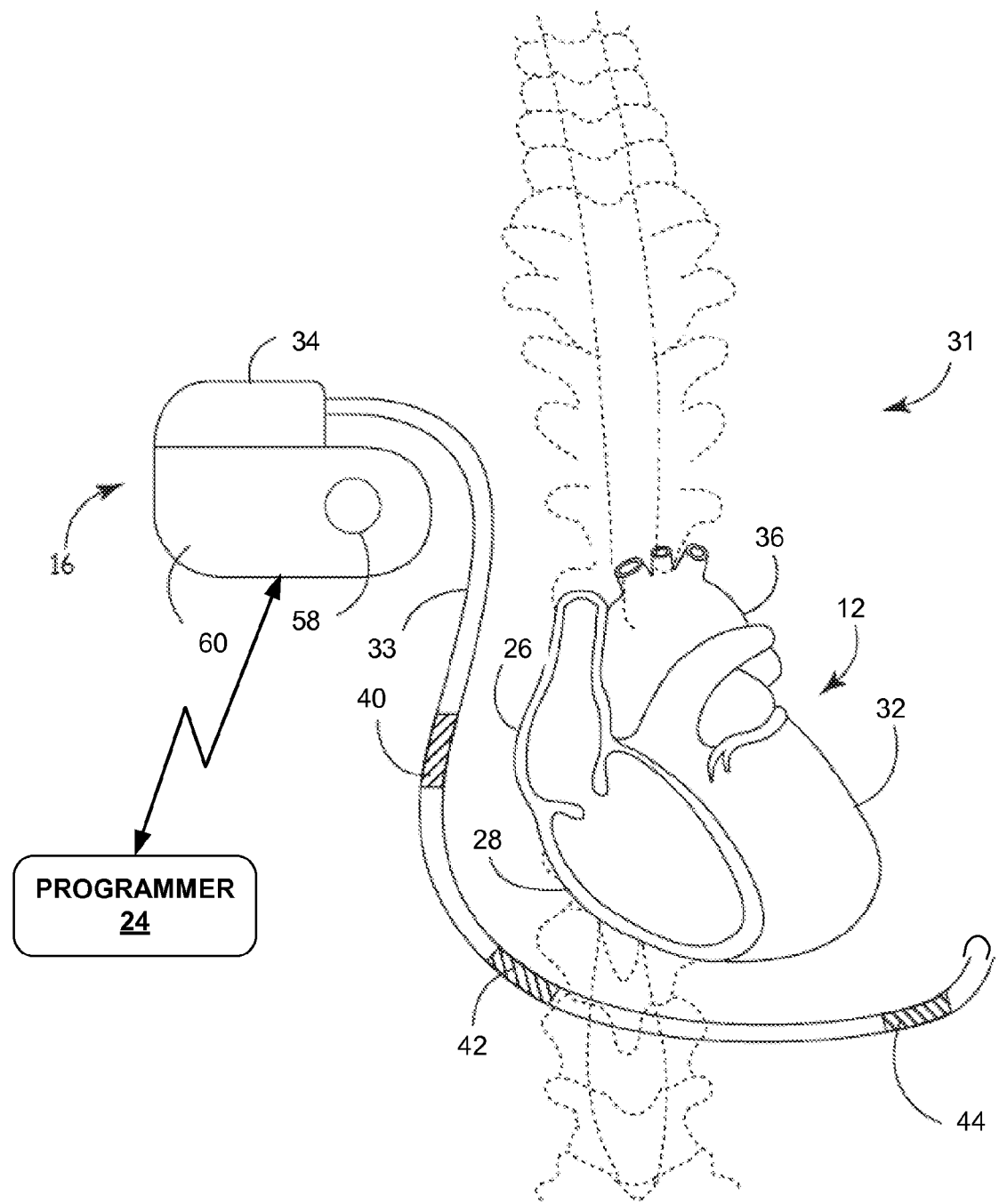
Figure 1C:
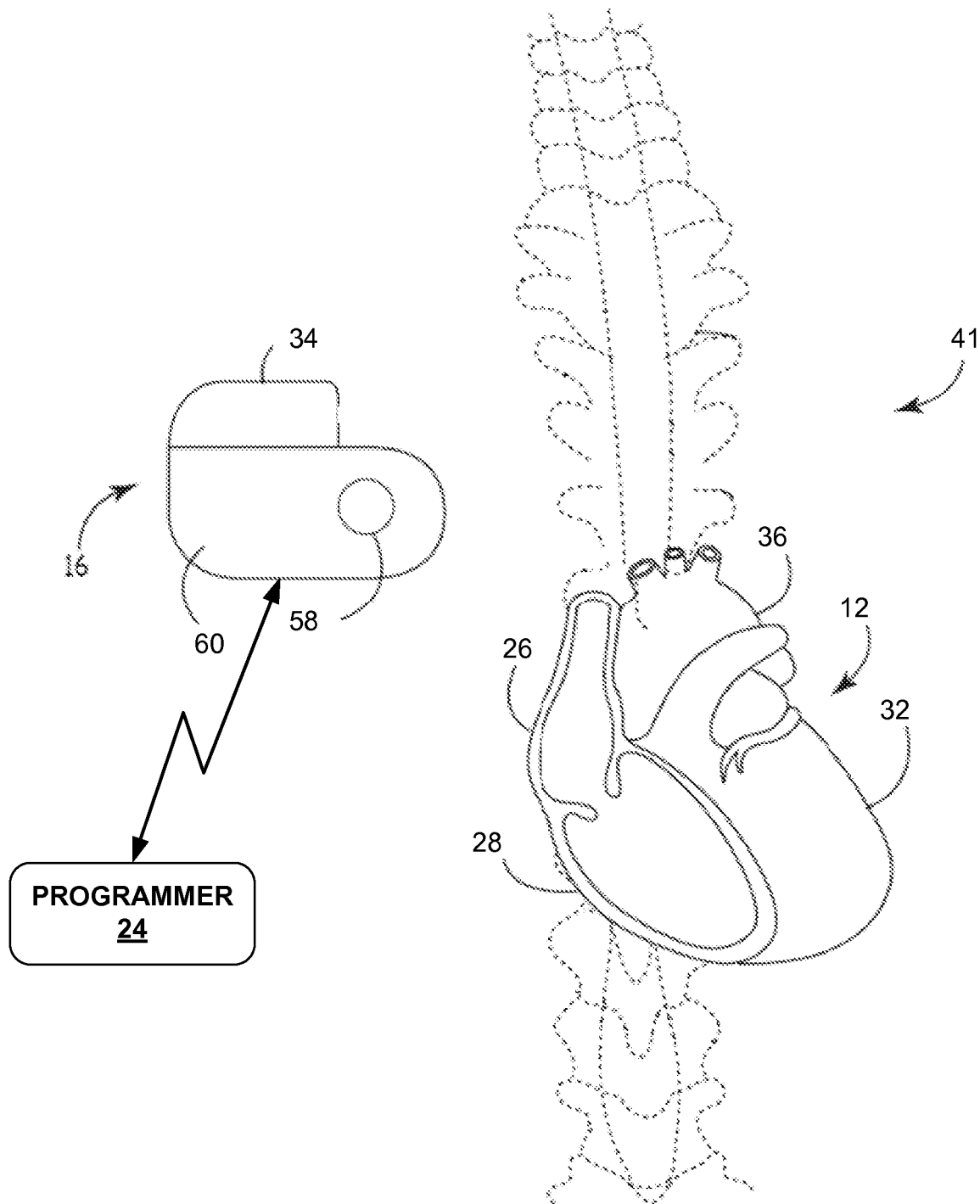

FIGS. 1A-1C illustrate example systems 10A, 10B, and 10C (collectively, "systems 10") that may be used for sensing of physiological parameters of a patient and/or to provide therapy to heart 12 of a patient. The systems may detect cardiac events, e.g., depolarizations and repolarizations, based on signals that the systems receive via electrodes. Each of the systems shown in FIGS. 1A-1C may be used for sensing of physiological parameters of a patient, and some of the systems may be used to provide therapy to heart 12 of the patient. The patient is ordinarily, but not necessarily, a human patient.

Each of systems 10A, 10B and 10C includes a respective implantable medical device (IMD) 16A, 16B, and 16C (collectively "IMDs 16"). IMDs 16 include or are coupled to electrodes, e.g., via multiple leads with electrodes or sensors on each lead (e.g., FIG. 1A), or one lead with multiple sensors or electrodes (e.g., FIG. 1B). FIG. 1C illustrates an IMD 16B that includes multiple electrodes, and may be leadless. IMDs 16 may be also coupled to programmer 24.

IMDs 16A and 16B may be, for example, an implantable pacemaker, cardioverter, and/or defibrillator that provides electrical signals to heart 12 via electrodes coupled to leads. IMD 16C may be a cardiac monitor that monitors a rhythm of heart 12, such as a Reveal® Plus implantable cardiac monitor, commercially available from Medtronic Inc. of Minneapolis, Minn.

In the example of FIG. 1A, leads 18, 20, 22 extend into the heart 12 of a patient to sense electrical activity of heart 12 and/or deliver electrical stimulation to heart 12. In this example, right ventricular (RV) lead 18 extends through one or more veins, the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, system 10A may additionally or alternatively include one or more leads or lead segments (not shown in FIG. 1A) that deploy one or more electrodes within the vena cava or other vein. These electrodes may allow alternative electrical sensing configurations that may provide improved or supplemental sensing in some patients. Furthermore, in some examples, system 10A may additionally or alternatively include temporary or permanent epicardial or subcutaneous leads, instead of or in addition to transvenous, intracardiac leads 18, 20 and 22. Such leads may be used for one or more of cardiac sensing, pacing, or cardioversion/defibrillation.

IMD 16A may sense electrical signals attendant to the depolarization and repolarization of heart 12 via electrodes coupled to at least one of the leads 18, 20, 22. In some examples, IMD 16A provides pacing pulses to heart 12 based on the electrical signals sensed within heart 12. The configurations of electrodes used by IMD 16A for sensing and pacing may be unipolar or bipolar. IMD 16A may detect arrhythmia of heart 12, such as tachycardia or fibrillation of the atria 26 and 36 and/or ventricles 28 and 32, and may also provide defibrillation therapy and/or cardioversion therapy via electrodes located on at least one of the leads 18, 20, 22. In some examples, IMD 16A may be programmed to deliver a progression of therapies, e.g., pulses with increasing energy levels, until a fibrillation of heart 12 is stopped. IMD 16A may detect fibrillation employing one or more fibrillation detection techniques known in the art.

Leads 18, 20, 22 may be electrically coupled to a signal generator, e.g., stimulation generator, and a sensing module of IMD 16A via a connector block 34. In some examples, proximal ends of leads 18, 20, 22 may include electrical contacts that electrically couple to respective electrical contacts within connector block 34 of IMD 16A. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44 and 48 may take the form of ring electrodes, and electrodes 42, 46 and 50 may take the form of extendable helix tip electrodes mounted retractably within insulative electrode heads 52, 54 and 56, respectively. In other examples, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

In some examples, as illustrated in FIG. 1A, IMD 16A includes one or more housing electrodes, such as housing electrode 58, which may be formed integrally with an outer surface of hermetically-sealed housing 60 of IMD 16A or otherwise coupled to housing 60. In some examples, housing electrode 58 is defined by an uninsulated portion of an outward facing portion of housing 60 of IMD 16A. Other division between insulated and uninsulated portions of housing 60 may be employed to define two or more housing electrodes. In some examples, housing electrode 58 comprises substantially all of housing 60. Housing 60 may enclose a signal generator that generates therapeutic stimulation, such as cardiac pacing pulses and defibrillation shocks, as well as a sensing module for monitoring the rhythm of heart 12.

IMD 16A may sense electrical signals attendant to the depolarization and repolarization of heart 12 via electrodes 40, 42, 44, 46, 48, 50, 62, 64 and 66. The electrical signals are conducted to IMD 16A from the electrodes via the respective leads 18, 20, 22. IMD 16A may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58. The combination of electrodes used for sensing may be referred to as a sensing configuration.

In some examples, IMD 16A delivers pacing pulses via bipolar combinations of electrodes 40, 42, 44, 46, 48 and 50 to produce depolarization of cardiac tissue of heart 12. In some examples, IMD 16A delivers pacing pulses via any of electrodes 40, 42, 44, 46, 48 and 50 in combination with housing electrode 58 in a unipolar configuration. Furthermore, IMD 16A may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes. The combination of electrodes used for delivery of stimulation or sensing, their associated conductors and connectors, and any tissue or fluid between the electrodes, may define an electrical path.

The configuration of system 10A illustrated in FIG. 1A is merely one example. In other examples, a system may include epicardial leads and/or patch electrodes instead of or in addition to the transvenous leads 18, 20, 22 illustrated in FIG. 1A. Further, IMD 16A need not be implanted within the patient. In examples in which IMD 16A is not implanted in the patient, IMD 16A may deliver defibrillation pulses and other therapies to heart 12 via percutaneous leads that extend through the skin of the patient to a variety of positions within or outside of heart 12.

In addition, in other examples, a system may include any suitable number of leads coupled to an IMD 16, and each of the leads may extend to any location within or proximate to heart 12. For example, other examples of systems may include three transvenous leads located as illustrated in FIG. 1A, and an additional lead located within or proximate to left atrium 36. As another example, other examples of systems may include a single lead that extends from an IMD 16 into right atrium 26 or right ventricle 28, or two leads that extend into a respective one of the right ventricle 28 and right atrium 26.

In some examples, programmer 24 comprises a handheld computing device, computer workstation, or networked computing device. Programmer 24 may include a user interface that receives input from a user. It should be noted that the user may also interact with programmer 24 remotely via a networked computing device.

A user, such as a physician, technician, surgeon, electrophysiologist, or other clinician, may interact with programmer 24 to communicate with IMD 16A. For example, the user may interact with programmer 24 to retrieve physiological or diagnostic information from IMD 16A. A user may also interact with programmer 24 to program IMD 16A, e.g., select values for operational parameters of the IMD.

For example, the user may use programmer 24 to retrieve information from IMD 16A regarding the rhythm of heart 12, trends therein over time, or arrhythmic episodes. As another example, the user may use programmer 24 to retrieve information from IMD 16A regarding other sensed physiological parameters of a patient, such as intracardiac or intravascular pressure, activity, posture, respiration, or thoracic impedance. As another example, the user may use programmer 24 to retrieve information from IMD 16A regarding the performance or integrity of the IMD 16A or other components of system 10A, such as leads 18, 20 and 22, or a power source of IMD 16A. In some examples, this information may be presented to the user as an alert. For example, asystole detection according to the techniques described herein may trigger IMD 16A to transmit an alert to the user via programmer 24.

IMD 16A and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16A implant site in order to improve the quality or security of communication between IMD 16A and programmer 24.

FIG. 1B is a conceptual diagram illustrating an example subcutaneous system 10B that may be used for sensing of physiological parameters of a patient and/or to provide therapy to heart 12 of a patient. The signal detection and processing techniques of this disclosure may be utilized by systems such as the systems of FIGS. 1A-1C, for example. System 10B includes IMD 16B and lead 33, which includes electrodes 41, 43, and 45. In the example illustrated in FIG. 1B, lead 33 is positioned within the patient such that electrodes 41, 43, and 45 are proximate to heart 12. In this way, IMD 16B may deliver electrical stimulation therapy to heart 12 via at least electrodes 41, 43, and 45 of lead 33. As described with respect to FIG. 1A, IMD 16B may include one or more housing electrodes, such as housing electrode 58, which may also deliver electrical stimulation therapy to heart 12.

In the example illustrated in FIG. 1B, electrodes 41, 43, and 45 are implanted proximate to, but outside of heart 12, e.g., in or under subcutaneous tissue outside of the ribcage. Electrodes 41, 43, and 45 may be referred to as extravascular electrodes. An extravascular electrode may comprise an electrode that is not implanted within heart 12 or within an artery or other vasculature of the patient. For example, electrodes 41, 43, and 45 may comprise subcutaneous, submuscular, epicardial, and/or intramural electrodes.

IMD 16B may deliver pacing pulses via any combination of electrodes 41, 43, and 45 and housing electrode 58, e.g., any unipolar or bipolar electrode configuration, to cause depolarization of cardiac tissue of heart 12. IMD 16B may alternatively or additionally deliver defibrillation and/or cardioversion pulses to heart 12 via electrodes 41, 43, 45, and 58. Electrodes 41, 43, and 45 may comprise elongated electrodes that take the form of coil electrodes. Such coil electrodes may be useful in delivering high energy defibrillation pulses to heart 12.

The number, configuration, and type of electrodes 41, 43, 45, and 58 shown in FIG. 1B are merely exemplary. In other examples, lead 33 may include any number, configuration, and type of electrodes 41, 43, and 45. For example, lead 33 may include one or more additional electrodes proximate to heart 12, e.g., proximate to left atrium 36. In the example illustrated in FIG. 1B, system 31 includes a single lead 33. In other examples, system 31 may include two or more leads.

As another example, a system may include both electrodes positioned within heart 12, as illustrated in system 10A of FIG. 1A, and electrodes positioned outside of heart 12, as illustrated in system 10B of FIG. 1B. As another example, a system may not include any leads. Instead, a system may sense physiological parameters of the patient and/or to provide therapy to heart 12 of the patient via a plurality of housing electrodes. Housing electrodes, such as housing electrode 58, may, for example, be formed integrally with an outer surface of hermetically-sealed housing 60 of IMD 16B or otherwise coupled to housing 60.

FIG. 1C is a conceptual diagram illustrating another example of subcutaneous system 10C, which is similar to system 10B of FIG. 1B, but is leadless. System 10C may be used for sensing of physiological parameters of a patient and/or to provide therapy to heart 12 of a patient. IMD 16C of system 10C may include a plurality of electrodes 58A, 58B and 58C (collectively "electrodes 58") formed on or integral with its housing for sensing cardiac electrical activity of a patient's heart. The number of electrodes 58 on the housing of IMD 16C is merely an example, and IMD 16C may include more or fewer electrodes 58. IMD 16C may be useful for physiological sensing and determining when false asystole detection occurs based on characteristics of a signal associated with cardiac activity, as described herein. In one example, IMD 16C may be a cardiac monitor that monitors a rhythm of heart 12, such as a Reveal® Plus implantable cardiac monitor, commercially available from Medtronic Inc. of Minneapolis, Minn.

Figure 2:
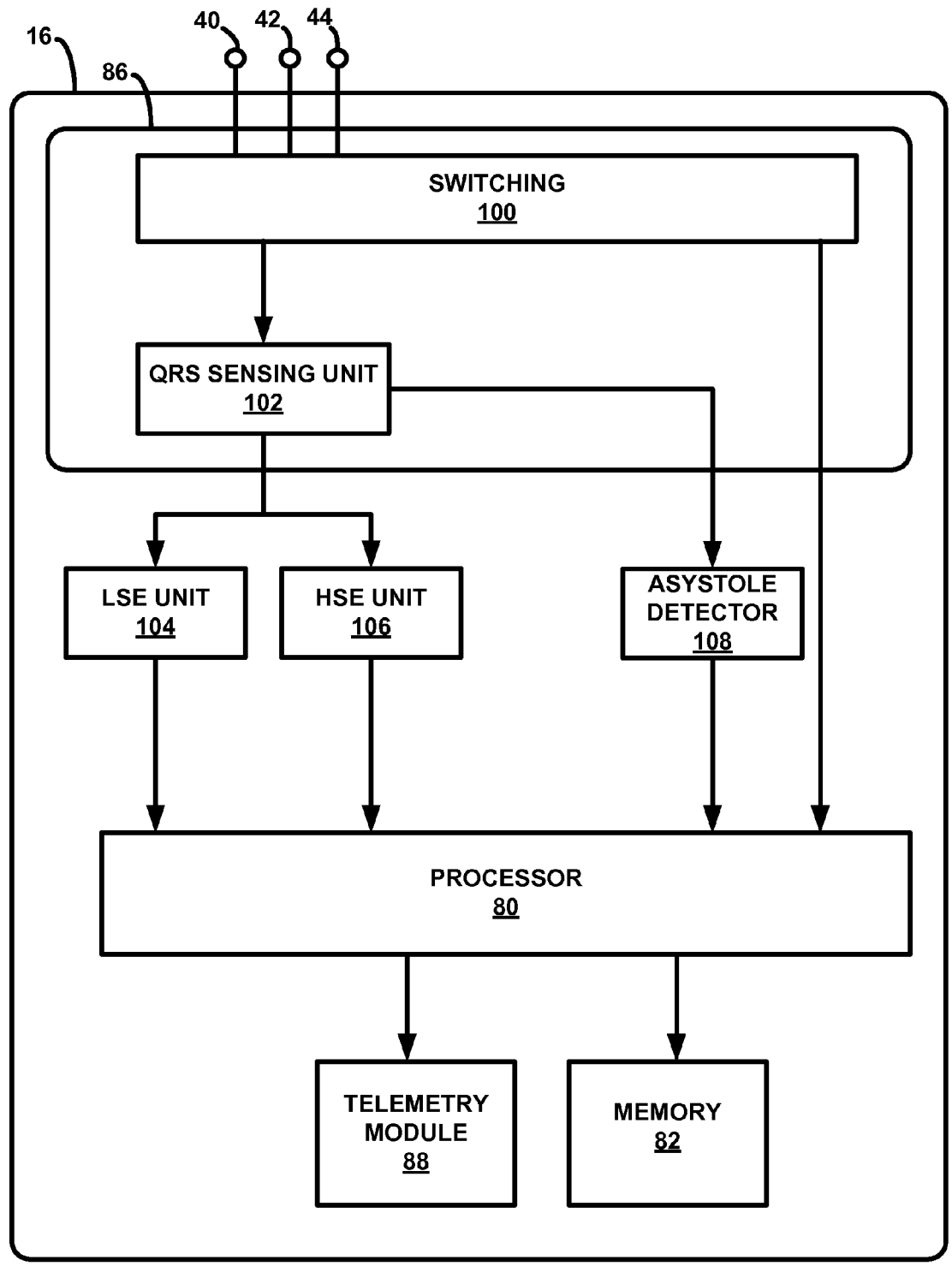
FIG. 2 is a functional block diagram illustrating an example configuration of the IMD of FIG. 1C.

FIG. 2 is a functional block diagram illustrating an example configuration of IMD 16C. IMDs 16A and 16B may be similarly configured, and may include the same or similar components as those illustrated in FIG. 2 with respect to IMD 16C.

In the illustrated example, IMD 16C includes a processor 80, memory 82, sensing module 86, and telemetry module 88. Memory 82 includes computer-readable instructions that, when executed by processor 80, cause IMD 16C and processor 80 to perform various functions attributed to IMD 16C and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Sensing module 86 monitors signals from electrodes 58, in order to monitor electrical activity of heart 12. Sensing module 86 may also include a switching module 100 to select which of the available electrodes 58 are used to sense the heart activity, depending upon which electrode combination is used in the current sensing configuration. In some examples, processor 80 may select the electrodes that function as sense electrodes, i.e., select the sensing configuration, via the switching module 100 within sensing module 86.

Sensing module 86 may include one or more detection channels, each of which may be coupled to a selected electrode configuration for detection of cardiac signals, e.g., receipt of an ECG, via that electrode configuration. Some detection channels may be configured to detect cardiac events within the ECG signal, such as P-waves or R-waves, and provide indications of the occurrences of such events to processor 80, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. One or more other detection channels may provide the signals to an analog-to-digital converter, for processing or analysis by processor 80.

Processor 80 may control the functionality of sensing module 86 by providing signals via a data/address bus. In some examples, processor 80 may further process signals that sensing module 86 detects. In some examples, processor 80 may transmit signals that sensing module 86 detects to another device for processing. Sensing module 86 may comprise circuitry that rectifies a sensed signal, e.g., ECG, to make determinations regarding occurrence of certain cardiac events based on the rectified detected signal.

In one example, processor 80 may execute algorithms that cause processor 80 to determine occurrence of certain cardiac events based on signals sensed by sensing module 86. For example, processor 80 may determine occurrence of an asystole or bradycardia when processor 80 determines that a threshold period of time has passed from detection of an R-wave by a channel of sensing module 86 prior to indication of another R-wave by the channel of sensing module 86. In one example, if the amplitude of R-waves in an ECG falls below a certain sensing threshold for a detection channel of sensing module 86 and remains below the threshold for a specified amount of time, processor 80 may incorrectly determine that an asystole or bradycardia has occurred, e.g., due to lack of indications of R-waves from the detection channel of the sensing module. In another example, if the amplitude of detected R-waves has a sudden increase (e.g., caused by a premature ventricular contraction (PVC)), the sensing threshold of the R-wave detection channel may be adjusted to a higher value based on the sensed high R-wave peak value, therefore, causing undersensing of the subsequent R-waves, and processor 80 may incorrectly determine that an asystole or bradycardia has occurred. Using techniques of this disclosure, processor 80 may determine based on amplitudes of detected R-waves when a detected asystole or bradycardia is false, as discussed in more detail below.

Processor 80 may include a timing and control module, which may be embodied as hardware, firmware, software, or any combination thereof. The timing and control module may comprise a dedicated hardware circuit, such as an ASIC, separate from other processor 80 components, such as a microprocessor, or a software module executed by a component of processor 80, which may be a microprocessor or ASIC. The timing and control module may implement programmable counters.

Intervals defined by the timing and control module within processor 80 may include refractory periods during which sensed P-waves and R-waves are ineffective to restart timing of the escape intervals. The durations of these intervals may be determined by processor 80 in response to stored data in memory 82.

Interval counters implemented by the timing and control module of processor 80 may be reset upon sensing of R-waves and P-waves with detection channels of sensing module 86. The value of the count present in the interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a tachyarrhythmia event, such as VF or VT. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by processor 80 in other examples.

In some examples, processor 80 may determine that tachyarrhythmia has occurred by identification of shortened R-R (or P-P) interval lengths. Generally, processor 80 detects tachycardia when the interval length falls below 360 milliseconds (ms) and fibrillation when the interval length falls below 320 ms. These interval lengths are merely examples, and a user may define the interval lengths as desired, which may then be stored within memory 82. This interval length may need to be detected for a certain number of consecutive cycles, for a certain percentage of cycles within a running window, or a running average for a certain number of cardiac cycles, as examples.

In some examples, processor 80 detects asystole and/or bradycardia based on value of an R-R or P-P interval counter. For example, when the value in the interval counter exceeds a threshold value, processor 80 may determine that asystole or bradycardia has occurred.

As described in greater detail below, IMD 16C, and more particularly processor 80, may be configured to determine, based on characteristics of the R-waves, whether a detected asystole or bradycardia is false. In response to determining false detection of an asystole or bradycardia (e.g., due to undersensing of a low amplitude signal or undersensing due to a modified threshold caused by a sudden increase in the amplitude of an R-wave), processor 80 may take one or more actions. In one example, processor 80 may not increment an event (e.g., asystole or bradycardia) counter, or the like. In other examples, processor 80 may withhold application of stimulation therapy normally applied following detection of asystole or bradycardia. In another example, processor 80 may utilize the false detection of asystole for diagnostic purposes, for example, to send an alert regarding possible causes of the falsely-detected asystole (e.g., shifting of a sensor or an outside source that may be interfering with the sensed signal).

In some examples according to this disclosure, processor 80 may employ algorithms to collect and evaluate amplitudes of R-waves during normal operation and make a determination regarding a detected asystole or bradycardia based on the evaluated amplitudes. In one example, processor 80 may determine whether during normal operation the amplitude of R-waves is consistently low. In this example, based on the number of R-waves detected with amplitude below a certain threshold, processor 80 may determine a detected asystole or bradycardia to be false. In another example, processor 80 may determine whether the amplitude of an R-wave is a sudden increase compared to previous R-waves. In this example, processor 80 may determine a detected asystole or bradycardia to be false if there is a sudden increase in R-wave amplitude. In both examples, if processor 80 determines that the detected asystole is not false, the asystole is confirmed. These techniques will be discussed in more detail below. In one example, if processor 80 determines that a detected asystole is false, processor 80 may store an indication (e.g., a low confidence detection flag) or store a diagnostic associated with the detected asystole (e.g., a count of occurrence of falsely-detected asystole). In another example, if processor 80 confirms a detected asystole, processor 80 may store diagnostics associated with the confirmed detected asystole (e.g., duration, timing of occurrence, rhythm preceding and following the asystole, and the like) for subsequent review by a clinician/physician, take an action (e.g., deliver therapy), or send an alert to a clinician/physician.

In some examples, processor 80 may provide an alert to a user, e.g., of programmer 24, regarding any detected asystole or bradycardia via telemetry module 88. Additionally, processor 80 may provide the ECG or other sensed signal to an external device, e.g., programmer 24, via telemetry module 88 for further evaluation of the detected asystole or bradycardia.

Telemetry module 88 includes any suitable hardware, firmware, software or any combination thereof for communicating with another device, such as programmer 24 (FIGS. 1A-1C). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, IMD 16C may signal programmer 24 to further communicate with and pass alerts regarding a detected asystole through a network such as the Medtronic CareLink® Network developed by Medtronic, Inc., of Minneapolis, Minn., or some other network linking patient 14 to a clinician.

In the illustrated example, sensing module 86 includes a QRS sensing unit 102, which may include a rectifier, a bandpass filter, and a threshold. Furthermore, IMD 16 includes a low signal evidence (LSE) counter 104, high signal evidence (HSE) flag 106, and asystole detector 108. LSE counter 104, HSE flag 106, and asystole detector 108 may be implemented as hardware, firmware, software, or any combination thereof. In some examples, LSE counter 104, HSE flag 106, and asystole detector 108 may be implemented in processor 80, e.g., may be firmware or software modules executed by processor 80. In other examples, all, or some subset of the components of sensing module 86, such as LSE counter 104 and HSE flag 106, may be implemented in another device, such as an external programmer or other external computing device.

In some examples, sensing module 86 may include multiple channels, e.g., to process multiple signals simultaneously. For example, sensing module 86 may apply multiple signal processing techniques for asystole detection to multiple signals simultaneously. For example, sensing module 86 may simultaneously receive ECGs from multiple electrodes, which may be, for example, at spatially-distinct locations or subcutaneous ECGs and/or surface ECGs, and make determinations regarding cardiac events (e.g., asystole or bradycardia) based on each of the received signals. Applying asystole detection techniques to multiple ECGs may improve determination of a false asystole detection and subsequent therapy. Switching module 100 may, based on control signals from processor 80, control which of electrodes 58 coupled to which channels at any given time.

QRS sensing unit 102 may receive a signal indicative of cardiac activity, such as an ECG, from one or more of electrodes 58, and utilize a rectifier to rectify the signal, and provide the rectified signal to LSE counter 104, HSE flag 106, and asystole detector 108. In some examples, QRS sensing unit 102 may also utilize a bandpass filter that passes a range of frequencies based on the type of cardiac event, e.g., P- or R-wave, that sensing module 86 and, more particularly, the selected detection channel of sensing module 86 is configured to detect. In particular, QRS sensing unit 102 may pass frequencies that correlate with a selected type of cardiac event, e.g., P- or R-wave, and the amplitude of the filtered and rectified signal may vary according to how the signal amplitude in the frequency range that correlates with the selected type of cardiac event varies. As one example, QRS sensing unit 102 may pass frequencies within the range of approximately 13 Hertz (Hz) to approximately 39 Hz when the selected detection channel of sensing module 86 is configured to detect R-waves.

Asystole detector 108 may receive the rectified signal from QRS sensing unit 102 and analyze the signal to determine whether a certain cardiac event, e.g., asystole, has occurred. For example, asystole detector 108 may detect the R-wave peaks of the rectified signal. Asystole detector 108 may set a sensing floor threshold (e.g., 50 µV), which may correspond to a minimum value at which an R-wave peak may be detected. In the example of a low signal, the peak of a rectified R-wave falls below the sensing floor threshold, and asystole detector 108 does not detect the R-wave. If multiple consecutive R-wave peaks are below the sensing floor threshold, and therefore, asystole detector 108 does not detect a signal for a period of time, an asystole may be detected. Asystole detector 108 may detect an asystole if, for example, no signal is detected for at least 3 seconds. In the sudden increase in R-wave peak example, asystole detector 108 may sense the high amplitude R-wave peak and adjust the sensing floor threshold accordingly, e.g., from 50 µV to 100 µV, or from 1000 µV to 2000 µV. As a result, subsequent R-wave peaks, which would have otherwise been sensed, may fall below the adjusted sensing threshold, and as a result may not be detected by asystole detector 108. In one example, QRS sensing unit 102 may adjust the sensing threshold according to the detection methods described in U.S. Pat. No. 7,027,858 to Cao et al., entitled "METHODS AND APPARATUS FOR CARDIAC R-WAVE SENSING IN A SUBCUTANEOUS ECG WAVEFORM," which issued on Apr. 11, 2006, and is incorporated herein by reference in its entirety.

If asystole detector 108 does not detect a signal by not detecting R-wave peaks for a period of time, e.g., 3 seconds, asystole detector 108 detects an asystole. In some situations, a detected asystole in either example may be false. Processor 80 may receive an indication from asystole detector 108 that an asystole was detected.

LSE unit 104 may receive the rectified signal from QRS sensing unit 102 and analyze the signal to determine whether there is indication that the signal is low. LSE unit 104 may detect the R-wave peaks of the rectified signal and compare them to an LSE threshold. The LSE threshold may be a low threshold, which is larger than the sensing floor threshold. For each R-wave peak, LSE unit 104 may evaluate the amplitude of the R-wave peak. If the amplitude is below the LSE threshold, LSE unit 104 increments an LSE counter, and if the amplitude is above the LSE threshold, LSE unit 104 decrements the LSE counter. LSE unit 104 may send the LSE counter to processor 80 when processor 80 receives from asystole detector 108 an indication that asystole was detected.

HSE unit 10 may receive the rectified signal from rectified 102 and analyze the signal to determine whether there is indication that there was a sudden increase in R-wave peak amplitude in the signal. HSE unit 10 may detect the R-wave peaks of the rectified signal and compare the amplitude of each R-wave peak to the preceding R-wave peak. If the current R-wave peak amplitude is larger than X times the preceding R-wave peak amplitude, an HSE flag is set, and if it is not, the HSE flag is reset. HSE unit 106 may send the HSE flag to processor 80 when processor 80 receives from asystole detector 108 an indication that asystole was detected.

When processor 80 receives an indication of asystole detection from asystole detector 108, processor 80 may request that LSE unit 104 and HSE unit 106 send the LSE counter and the HSE flag, respectively. Based on the value of the LSE counter or the HSE flag, processor 80 determines whether the detected asystole is false or not. For example, if the value of the LSE counter is above a certain value, then the signal is low, and processor 80 ignores the detected asystole. In another example, if the HSE flag is set, then there was a sudden increase in the R-wave peak amplitude, and processor 80 ignores the detected asystole. If the value of the LSE counter is below a certain value and the HSE flag is reset, processor 80 confirms the detected asystole and acts accordingly. In one example, if processor 80 confirms a detected asystole, processor 80 may store diagnostics associated with the confirmed detected asystole for subsequent review by a clinician/physician, take an action, or send an alert to a clinician/physician.

Figure 3:
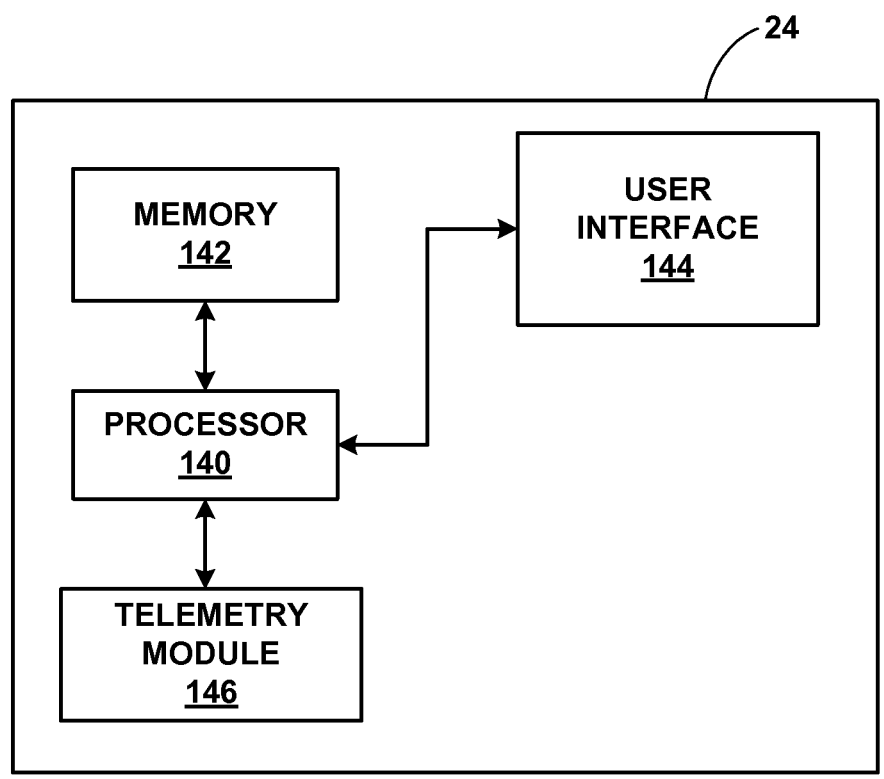
FIG. 3 is a functional block diagram illustrating an example configuration of an external programmer that facilitates user communication with an IMD.

FIG. 3 is functional block diagram illustrating an example configuration of programmer 24. As shown in FIG. 3, programmer 24 may include a processor 140, memory 142, user interface 144, telemetry module 146, and power source 148. Programmer 24 may be a dedicated hardware device with dedicated software for programming of IMDs 16. Alternatively, programmer 24 may be an off-the-shelf computing device running an application that enables programmer 24 to program IMDs 16.

A user may use programmer 24 to select therapy programs (e.g., sets of stimulation parameters), generate new therapy programs, modify therapy programs through individual or global adjustments or transmit the new programs to a medical device, such as IMDs 16. The clinician may interact with programmer 24 via user interface 144, which may include display to present graphical user interface to a user, and a keypad or another mechanism for receiving input from a user. In addition, the user may receive an alert from IMDs 16 indicating a detected asystole via programmer 24.

Processor 140 can take the form one or more microprocessors, DSPs, ASICs, FPGAs, programmable logic circuitry, or the like, and the functions attributed to processor 100 herein may be embodied as hardware, firmware, software or any combination thereof. Memory 142 may store instructions that cause processor 100 to provide the functionality ascribed to programmer 24 herein, and information used by processor 100 to provide the functionality ascribed to programmer 24 herein. Memory 142 may include any fixed or removable magnetic, optical, or electrical media, such as RAM, ROM, CD-ROM, hard or floppy magnetic disks, EEPROM, or the like. Memory 142 may also include a removable memory portion that may be used to provide memory updates or increases in memory capacities. A removable memory may also allow patient data to be easily transferred to another computing device, or to be removed before programmer 24 is used to program therapy for another patient.

Programmer 24 may communicate wirelessly with IMDs 16, such as using RF communication or proximal inductive interaction. This wireless communication is possible through the use of telemetry module 146, which may be coupled to an internal antenna or an external antenna. An external antenna that is coupled to programmer 24 may correspond to the programming head that may be placed over heart 12, as described above with reference to FIGS. 1A-1C. Telemetry module 146 may be similar to telemetry module 88 of IMD 16C (FIG. 2).

Telemetry module 146 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 140 of programmer 24 and/or one or more processors of one or more networked computers may perform all or a portion of the techniques described herein with respect to processor 80 and IMD 16. For example, processor 140 or another processor may receive an ECG or other sensed signal for identification of falsely-detected asystole.

Figure 4:
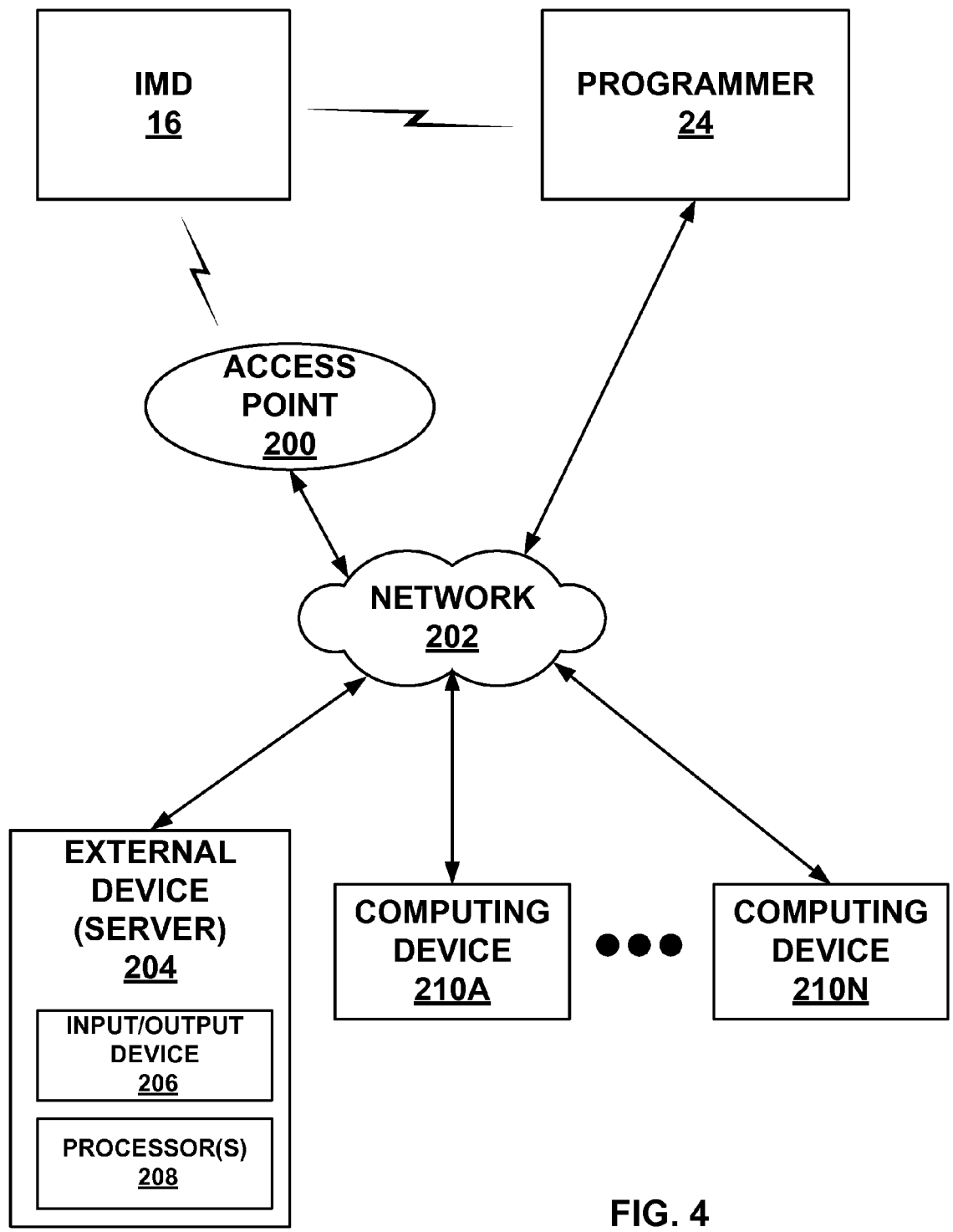
FIG. 4 is a block diagram illustrating an example system that includes an external device, such as a server, and one or more computing devices that are coupled to an IMD and a programmer via a network.

FIG. 4 is a block diagram illustrating an example system that includes an external device, such as a server 204, and one or more computing devices 210A-210N, that are coupled to the IMD 16 and programmer 24 shown in FIGS. 1A-1C via a network 202. In this example, IMD 16 may use its telemetry module 88 to communicate with programmer 24 via a first wireless connection, and to communication with an access point 200 via a second wireless connection. In the example of FIG. 4, access point 200, programmer 24, server 204, and computing devices 210A-210N are interconnected, and able to communicate with each other, through network 202. In some cases, one or more of access point 200, programmer 24, server 204, and computing devices 210A-210N may be coupled to network 202 through one or more wireless connections. IMD 16, programmer 24, server 204, and computing devices 210A-210N may each comprise one or more processors, such as one or more microprocessors, DSPs, ASICs, FPGAs, programmable logic circuitry, or the like, that may perform various functions and operations, such as those described herein.

Access point 200 may comprise a device that connects to network 202 via any of a variety of connections, such as telephone dial-up, digital subscriber line (DSL), or cable modem connections. In other examples, access point 200 may be coupled to network 202 through different forms of connections, including wired or wireless connections. In some examples, access point 200 may be co-located with a patient and may comprise one or more programming units and/or computing devices (e.g., one or more monitoring units) that may perform various functions and operations described herein. For example, access point 200 may include a home-monitoring unit that is co-located with the patient and that may monitor the activity of IMD 16. In some examples, server 204 or computing devices 210 may control or perform any of the various functions or operations described herein, e.g., determine whether a detected asystole or bradycardia is false based on an analysis of a cardiac signal received from IMD 16 or control determinations regarding detected asystole by IMD 16.

In some cases, server 204 may be configured to provide a secure storage site for archival of cardiac event detection information that has been collected from IMD 16 and/or programmer 24. Network 202 may comprise a local area network, wide area network, or global network, such as the Internet. In some cases, programmer 24 or server 204 may assemble sensing integrity information in web pages or other documents for viewing by and trained professionals, such as clinicians, via viewing terminals associated with computing devices 210. The system of FIG. 4 may be implemented, in some aspects, with general network technology and functionality similar to that provided by the Medtronic CareLink® Network developed by Medtronic, Inc., of Minneapolis, Minn.

Figure 5:
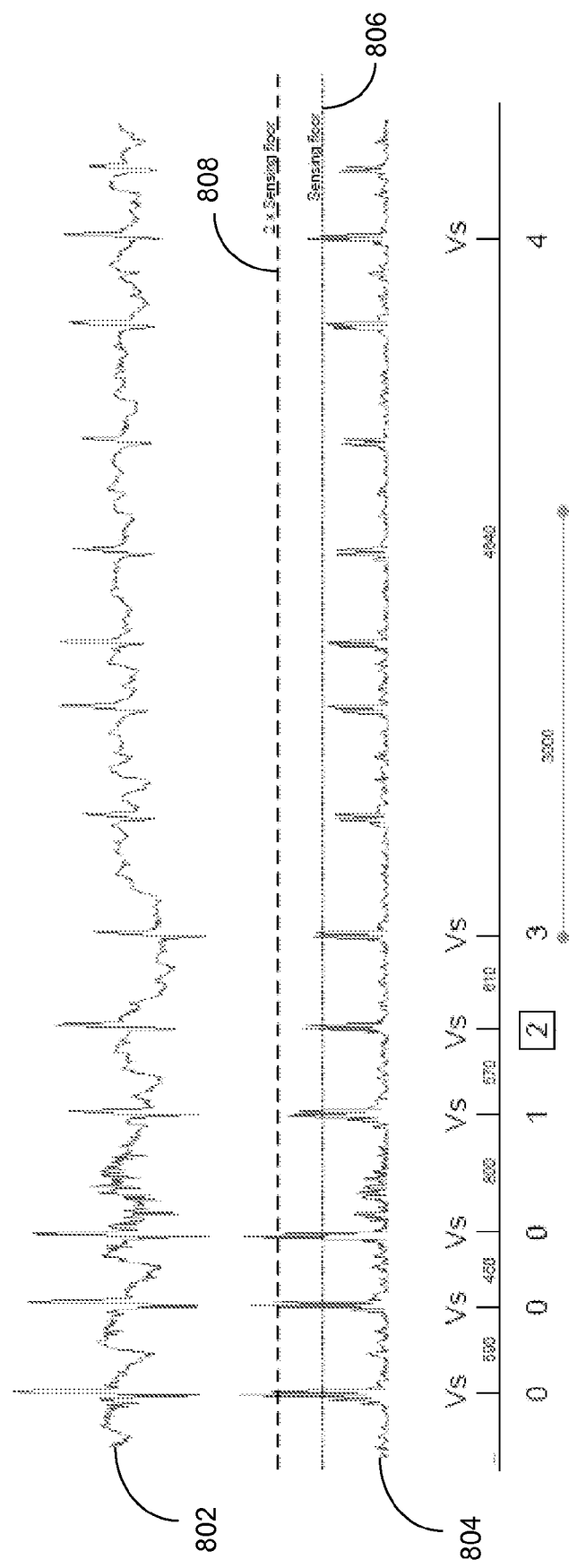
FIG. 5 illustrates an example ECG signal with a falsely-detected asystole due to a drop in signal amplitude.

FIG. 5 illustrates an example ECG signal with a falsely-detected asystole due to a drop in signal amplitude. In this example, a sensing device, e.g., IMD 16, may collect an ECG signal 802. The ECG signal may go through a rectifier, e.g., a rectifier of QRS sensing unit 102 of FIG. 2, which may filter and rectify ECG signal 802. The range of frequencies that the filtering passes may be based on the type of cardiac event of interest. In this example, the QRS sensing unit passes frequencies that correlate with detection of R-waves, resulting in a rectified ECG signal 804, where the peaks represent the R-wave peaks in the ECG signal. During normal operation, a processor (e.g., processor 80 and/or asystole detector 108) may sense R-wave peaks if their amplitude is above a certain minimal threshold or a sensing floor threshold, e.g., 35 or 50 µV. Any R-wave peaks below the sensing floor threshold remain undetected. If there are consecutive R-waves with peaks below sensing floor threshold 806 for a period longer than a specified amount of time, e.g., 3000 m seconds, a processor (e.g., processor 80 and/or asystole detector 108) may detect an asystole.

In accordance with techniques of this disclosure, a processor may execute an algorithm that determines whether a detected asystole is false. The processor may utilize a second threshold, e.g., LSE threshold 808, to determine whether there is evidence that the signal is exhibiting low amplitude characteristics. The second threshold may be calculated by, for example, multiplying sensing floor threshold 806 with a factor K, where K is greater than 1, or by adding a fixed value to sensing floor threshold 806. In the example of FIG. 5, LSE threshold 808 is a multiple of sensing floor threshold 806, where K is 2. The processor may compare each sensed R-wave peak (i.e., R-wave peaks above sensing floor threshold 806) to LSE threshold 808. If the amplitude of a sensed R-wave peak is below LSE threshold 808, the processor increments a counter, e.g., an LSE counter, and if the amplitude is above LSE threshold 808, the processor decrements the LSE counter. Initially, the LSE counter may be set to 0. In one example, the LSE counter may have maximum and minimum values (e.g., 10 and 0, respectively), above and below which the LSE counter may not go. When an asystole is detected, the processor checks the LSE counter, and if the value of the counter is at or above a predefined value, the processor determines that the detected asystole is false and the asystole is ignored. Otherwise, if the LSE counter is below the predefined value, the processor determines that the asystole was correctly-detected, and acts accordingly. In the example of FIG. 5, the predefined value is 1, therefore, if the LSE counter is 1 or higher, the processor indicates that the detected asystole is false.

Figure 6:
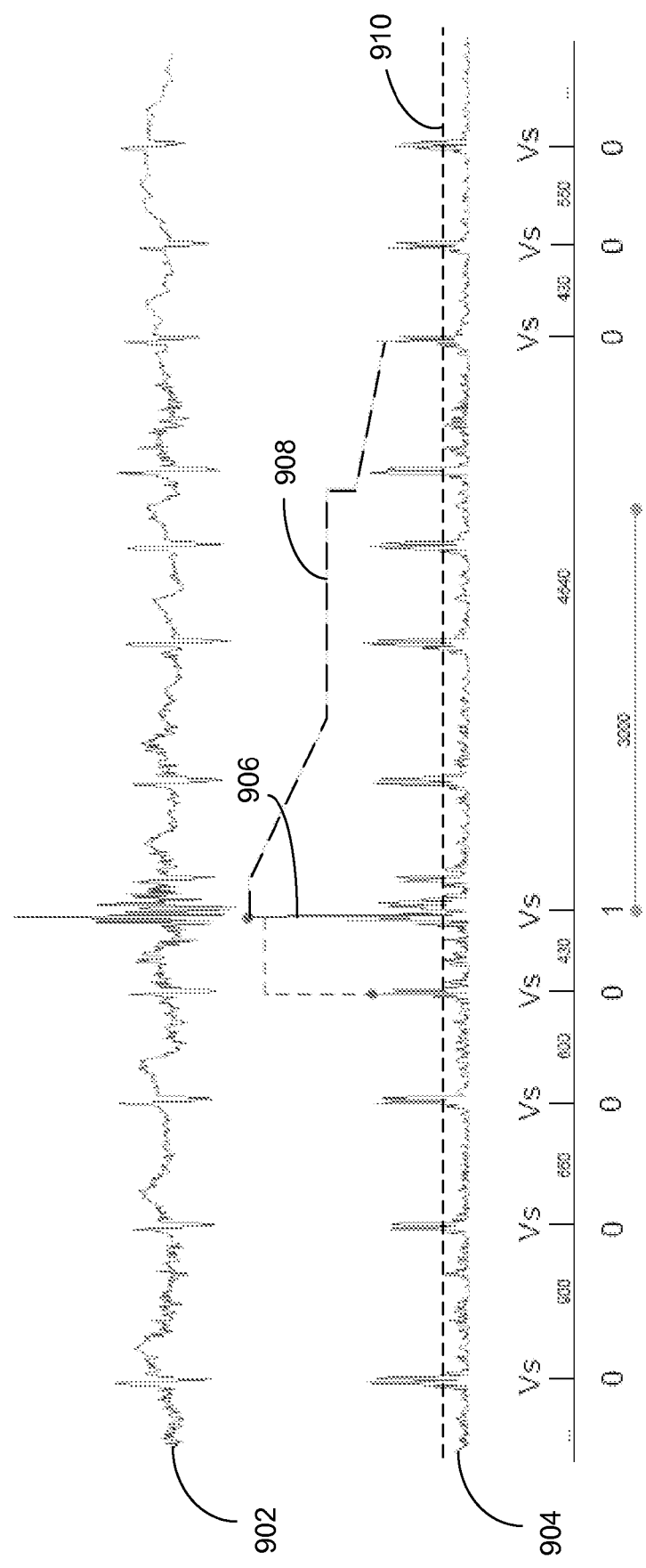
FIG. 6 illustrates an example ECG signal with a falsely-detected asystole due to a sudden increase in signal amplitude.

FIG. 6 illustrates an example ECG signal with a falsely-detected asystole due to a sudden increase in signal amplitude. In this example, a sensing device may collect an ECG signal 902. ECG signal 902 may go through a rectifier, e.g., a rectifier of QRS sensing unit 102 of FIG. 2, which may filter and rectify ECG signal 902, as explained above, resulting in rectified ECG signal 904, where the peaks represent the R-wave peaks in the ECG signal. During normal operation, a processor (e.g., processor 80 and/or asystole detector 108) may sense R-wave peaks if their amplitude is above a sensing floor threshold, e.g., 35 or 50 µV. In some examples, ECG signal 902 may experience a sudden increase, which may cause an R-wave peak amplitude to increase suddenly to a higher value than the neighboring R-wave peaks. In some examples, a sudden increase in the amplitude of an R-wave peak may cause the system to readjust the sensing floor threshold by increasing it to accommodate the high amplitude. As FIG. 6 shows, a sudden high amplitude R-wave peak 906, results in an adjusted higher sensing threshold 908 (relative to the sensing floor threshold 910), which causes under-sensing of the R-wave peaks that follow the high R-wave peak 906. As a result, the R-wave peaks that follow R-wave peak 906 may not be sensed for a specified period of time that results in detecting asystole.

In accordance with techniques of this disclosure, a processor may execute an algorithm that determines whether a detected asystole is false. The processor may compare each sensed R-wave peak amplitude to the amplitude of the preceding R-wave peak. If the current sensed R-wave peak amplitude is larger than the previous sensed R-wave peak amplitude multiplied by a factor H, a flag, e.g., HSE flag, is set to 1 to indicate the presence of a high signal, otherwise, the HSE flag is reset to 0. In one example, factor H may be set to 2, therefore, indicating a high signal when the amplitude of an R-wave peak is twice the amplitude of the previous R-wave peak amplitude. When an asystole is detected, the processor checks the HSE flag, and if the value of the flag is 1, the processor determines that the detected asystole is false and the asystole is ignored. Otherwise, if the HSE flag is 0, the processor determines that the asystole was correctly-detected, and acts accordingly.

Figure 7:
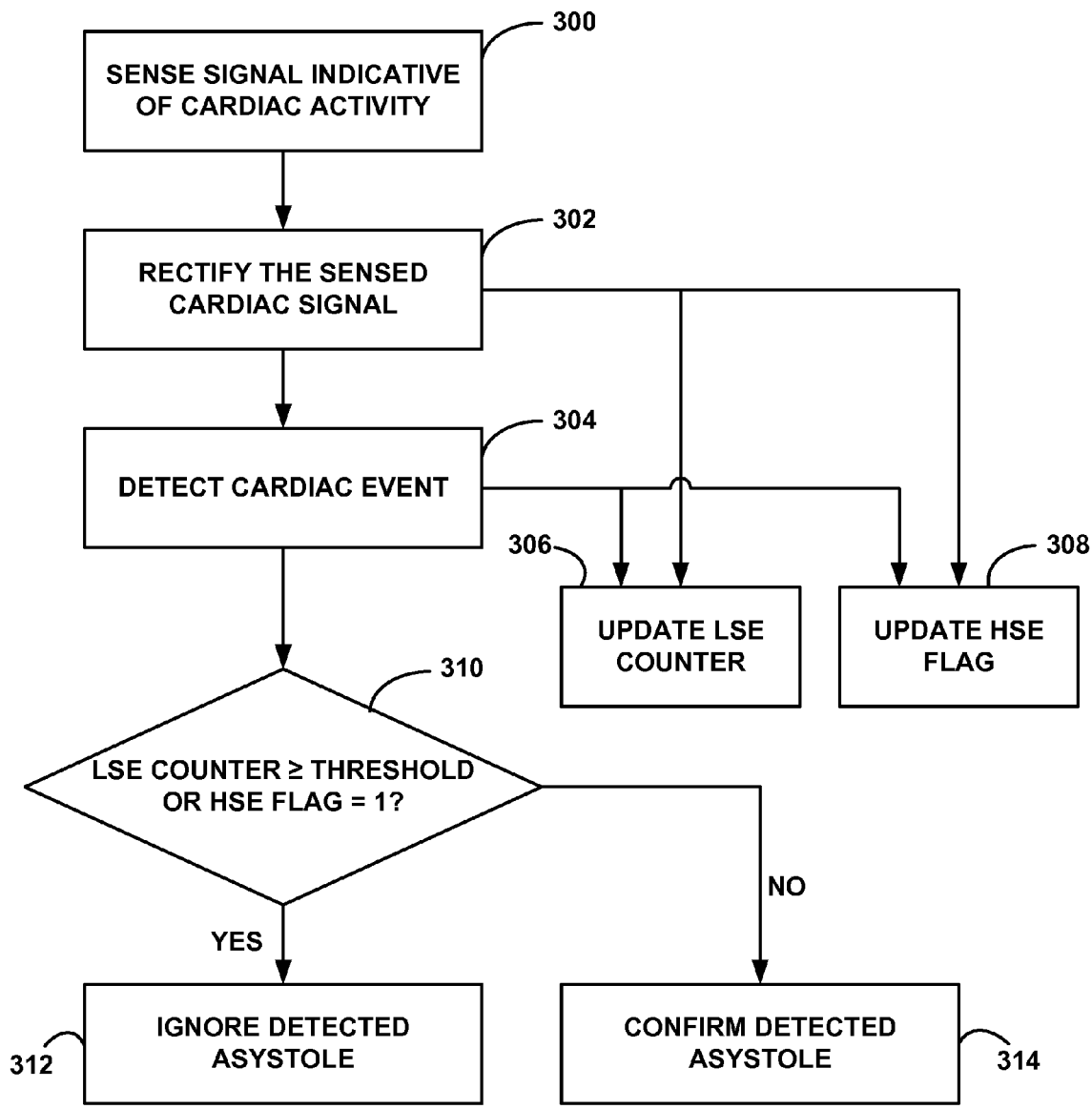
FIG. 7 is a flow diagram of an example method of determining whether detection of asystole is false.

FIG. 7 is a flow diagram of an example method of determining whether a detected asystole is false. Sensing module 86 senses a signal indicative of cardiac activity, such as an ECG, from a combination of two or more of electrodes 58 (300). QRS sensing unit 102 rectifies the sensed cardiac signal (302). The QRS sensing unit may filter the signal, such that the frequencies that pass correspond to the R-wave portion of the signal, resulting in a sequence of amplified R-waves as illustrated in the examples of FIGS. 5 and 6.

Sensing module 86, and more particularly asystole detector 108, analyzes the rectified signal to detect occurrences of cardiac events, e.g., R-waves, P-waves, asystole, bradycardia, and tachyarrhythmia (304). For example, sensing module 86 may utilize a sensing threshold to determine presence of a signal, by detected R-wave peaks relative to the sensing threshold. If an R-wave peak has amplitude lower than the sensing threshold, the R-wave is not detected. When consecutive R-wave peaks are not detected for a specified period of time, e.g., 3 seconds, asystole detector 108 determines that an asystole has occurred and indicates detection of asystole to a processor, e.g., processor 80.

Sensing module 86 may analyze the rectified cardiac signal to monitor certain characteristics associated with the signal. In one example, the characteristics of the signal may indicate that the signal is exhibiting low signal behavior, where R-wave peaks may have lower amplitudes than normal, which may be caused by a shift in electrode positioning or an outside interfering signal, for example. Therefore, R-wave peaks that fall below the sensing threshold may not be truly that low, thus, a detected asystole may be false. LSE unit 104 may execute an algorithm that updates a value that may indicate whether the signal is low, e.g., an LSE counter (306). For each R-wave peak, LSE unit 104 may evaluate the amplitude of the R-wave peak. If the amplitude is below the LSE threshold, LSE unit 104 increments the LSE counter, and if the amplitude is above the LSE threshold, LSE unit 104 decrements the LSE counter. The LSE threshold may be the sensing threshold multiplied by a factor larger than 1 (e.g., 2) or the sensing threshold plus a constant value. Initially, the LSE counter may be set to 0, and it may have a maximum and minimum value above and below which the LSE counter value may not go.

In another example, the characteristics of the signal may indicate a signal behavior that shows a sudden increase in amplitude, where one R-wave peak may have a sudden increase in peak amplitude relative to neighboring R-wave peaks. The sudden amplitude increase may cause adjustment to the sensing threshold by increasing the sensing threshold, causing undersensing of subsequent R-wave peaks, which would otherwise be detected, and resulting in a falsely-detected asystole. HSE unit 106 may execute an algorithm that updates a value that may indicate whether the signal experienced a sudden increase in amplitude, e.g., an HSE flag (308). HSE unit 10 may compare the amplitude of each R-wave peak to the preceding R-wave peak. If the current R-wave peak amplitude is larger than X times the preceding R-wave peak amplitude, the HSE flag is set, and if it is not, the HSE flag is reset.

When processor 80 detects or receives indication that a cardiac event was detected (304), e.g., asystole, processor 80 may retrieve from LSE unit 104 and HSE unit 106 the LSE counter and the HSE flag, respectively. Processor 80 may check the values of the LSE counter and the HSE flag (310). Based on the value of the LSE counter or the HSE flag, processor 80 determines whether the detected asystole is false or not. For example, if the value of the LSE counter is equal to or above a certain threshold value (e.g., 1), indicating the signal is low, or if the HSE flag is set, indicating there was a sudden increase in amplitude in the signal, processor 80 ignores the detected asystole (312). If the value of the LSE counter is below the threshold value and the HSE flag is reset, processor 80 confirms the detected asystole and acts accordingly (314).

Although the disclosure is described with respect to systems that employ sensing and monitoring of cardiac activity, such techniques may be applicable to other systems in which sensing integrity is important, such as, e.g., spinal cord stimulation, deep brain stimulation, pelvic floor stimulation, gastric stimulation, occipital stimulation, functional electrical stimulation, and the like.

The techniques described in this disclosure, including those attributed to image IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples of the invention have been described. These and other examples are within the scope of the following claims.

The invention claimed is:

1. A method comprising: sensing an electrocardiogram signal; comparing an amplitude of the signal to a first threshold; detecting at least one of an asystole or a bradycardia based on the comparison of the amplitude of the signal to the first threshold; in response to detecting at least one of the asystole or the bradycardia, comparing an amplitude of at least one R-wave detected in the signal to at least a second threshold, the at least one R-wave detected based on comparison of the amplitude of the signal to the first threshold; and determining whether the detection of the asystole or the bradycardia is false based on the comparison of the amplitude of the detected R-wave to the at least second threshold.

2. The method of claim 1, further comprising rectifying the sensed signal.

3. The method of claim 1, wherein the signal comprises a rectified electrocardiogram (ECG).

4. The method of claim 1, wherein determining whether the detection of the asystole or the bradycardia is false comprises:
   determining whether the amplitude of the R-wave is below the at least second threshold; and incrementing a counter value if the amplitude of the R-wave is below the at least second threshold and decrementing the counter value if the amplitude of the R-wave is above the at least second threshold, wherein the detection of the asystole or the bradycardia is false if the counter value is above a threshold counter value.

5. The method of claim 1, further comprising:
   determining the at least second threshold based on a multiple of an amplitude of a previous R-wave, wherein determining whether the detection of the asystole or the bradycardia is false comprises:
      setting a flag value to a first value if the amplitude of the R-wave is greater than the at least second threshold and to a second value if the amplitude of the R-wave is less than the at least second threshold; and
      determining that the detection of the asystole or the bradycardia is false if the flag value is set to the first value.

6. The method of claim 1, further comprising:
   determining at least a third threshold based on a multiple of an amplitude of a previous R-wave, wherein determining whether the detection of the asystole or the bradycardia is false comprises:
      determining whether the amplitude of the R-wave is below the at least second threshold;
      incrementing a counter value if the amplitude of the R-wave is below the second threshold and decrementing the counter value if the amplitude of the R-wave is above the second threshold;
      setting a flag value to a first value if the amplitude of the R-wave is greater than the at least third threshold and to a second value if the amplitude of the R-wave is less than the at least third threshold; and
      determining that the detection of the asystole or the bradycardia is false if the counter value is above a threshold counter value or if the flag value is set to the first value.

7. A medical system comprising: a sensing module that senses an electrocardiogram signal; a detector module that compares an amplitude of the signal to a first threshold, and detects at least one of an asystole or a bradycardia based on the comparison of the amplitude of the signal to the first threshold; at least a first comparison module that, in response to detecting at least one of the asystole or the bradycardia, compares an amplitude of at least one R-wave detected in the signal to at least a second threshold, the at least one R-wave detected based on comparison of the amplitude of the signal to the first threshold; and a processor that determines whether the detection of the asystole or the bradycardia is false based on the comparison of the amplitude of the detected R-wave to the at least second threshold by the at least first comparison module.

8. The medical system of claim 7, further comprising a rectifier that rectifies the sensed signal.

9. The medical system of claim 7, wherein the signal comprises a rectified electrocardiogram (ECG).

10. The medical system of claim 7, wherein the at least first comparison module determines whether the amplitude the R-wave is below the at least second threshold, and increments a counter value if the amplitude of the R-wave is below the at least second threshold and decrements the counter value if the amplitude of the R-wave is above the at least second threshold, wherein the processor determines that the detection of the asystole or the bradycardia is false if the counter value is above a threshold counter value.

11. The medical system of claim 7, wherein the at least first comparison module determines the at least second threshold based on a multiple of an amplitude of a previous R-wave, sets a flag value to a first value if the amplitude of the R-wave is greater than the at least second threshold and to a second value if the amplitude of the R-wave is less than the at least second threshold, wherein the processor determines that the detection of the asystole or the bradycardia is false if the flag value is set to the first value.

12. The medical system of claim 7, further comprising at least a second comparison module, wherein the at least first comparison module determines whether the amplitude of the R-wave is below the at least second threshold, and increments a counter value if the amplitude of the R-wave is below the at least second threshold and decrements the counter value if the amplitude of the R-wave is above the at least second threshold, wherein the at least second comparison module determines at least a third threshold based on a multiple of an amplitude of a previous R-wave, and sets a flag value to a first value if the amplitude of the R-wave is greater than the at least third threshold and to a second value if the amplitude of the R-wave is less than the at least third threshold, wherein the processor determines that the detection of the asystole or the bradycardia is false if the counter value is above a threshold counter value or if the flag value is set to the first value.

13. A medical system comprising: means for sensing an electrocardiogram signal; means for comparing an amplitude of the signal to a first threshold; means for detecting at least one of an asystole or a bradycardia based on the comparison of the amplitude of the signal to the first threshold; in response to detecting at least one of the asystole or the bradycardia, means for comparing an amplitude of at least one R-wave detected in the signal to at least a second threshold, the at least one R-wave detected based on comparison of the amplitude of the signal to the first threshold; and a means for determining whether the detection of the asystole or the bradycardia is false based on the comparison of the amplitude of the detected R-wave to the at least second threshold.

14. The medical system of claim 13, further comprising means for rectifying the sensed signal.

15. The medical system of claim 13, wherein the signal comprises a rectified electrocardiogram (ECG).

16. The medical system of claim 13, wherein the means for determining whether the detection of the asystole or the bradycardia is false comprises:
   means for determining whether the amplitude of the R-wave is below the at least second threshold; and
   means for incrementing a counter value if the amplitude of the R-wave is below the at least second threshold and decrementing the counter value if the amplitude of the R-wave is above the at least second threshold,
   wherein the detection of the asystole or the bradycardia is false if the counter value is above a threshold counter value.

17. The medical system of claim 13, further comprising:
   means for determining the at least second threshold based on a multiple of an amplitude of a previous R-wave,
   wherein the means for determining whether the detection of the asystole or the bradycardia is false comprises:
      means for setting a flag value to a first value if the amplitude of the R-wave is greater than the at least second threshold and to a second value if the amplitude of the R-wave is less than the at least second threshold; and means for determining that the detection of the asystole or the bradycardia is false if the flag value is set to the first value.

18. The medical system of claim 13, further comprising:
means for determining at least a third threshold based on a multiple of an amplitude of a previous R-wave, wherein the means for determining whether the detection of the asystole or the bradycardia is false comprises:
means for determining whether the amplitude of the R-wave is below the at least second threshold;
means for incrementing a counter value if the amplitude of the R-wave is below the second threshold and decrementing the counter value if the amplitude of the R-wave is above the second threshold;
means for setting a flag value to a first value if the amplitude of the R-wave is greater than the at least third threshold and to a second value if the amplitude of the R-wave is less than the at least third threshold; and
means for determining that the detection of the asystole or the bradycardia is false if the counter value is above a threshold counter value or if the flag value is set to the first value.

19. A non-transitory computer-readable medium comprising instructions, wherein the instructions cause a programmable processor to: sense an electrocardiogram signal; compare an amplitude of the signal to a first threshold; detect at least one of an asystole or a bradycardia based on the comparison of the amplitude of the signal to the first threshold; in response to detecting at least one of the asystole or the bradycardia, compare an amplitude of at least one R-wave detected in the signal to at least a second threshold, the at least one R-wave detected based on comparison of the amplitude of the signal to the first threshold; and determine whether the detection of the asystole or the bradycardia is false based on the comparison of the amplitude of the detected R-wave to the at least second threshold.

20. The non-transitory computer-readable medium of claim 19, further comprising instructions that cause the processor to rectify the sensed signal.

21. The non-transitory computer-readable medium of claim 19, wherein the signal comprises a rectified electrocardiogram (ECG).

22. The non-transitory computer-readable medium of claim 19, wherein the instructions to determine whether the detection of the asystole or the bradycardia is false comprise instructions that cause the processor to:
determine whether the amplitude of the R-wave is below the at least second threshold; and
increment a counter value if the amplitude of the R-wave is below the at least second threshold and decrement the counter value if the amplitude of the R-wave is above the at least second threshold,
wherein the detection of the asystole or the bradycardia is false if the counter value is above a threshold counter value.

23. The non-transitory computer-readable medium of claim 19, further comprising instructions that cause the processor to:
determine the at least second threshold based on a multiple of an amplitude of a previous R-wave, wherein the instructions to determine whether the detection of the asystole or the bradycardia is false comprise instructions that cause the processor to:
set a flag value to a first value if the amplitude of the R-wave is greater than the at least second threshold and to a second value if the amplitude of the R-wave is less than the at least second threshold; and
determine that the detection of the asystole or the bradycardia is false if the flag value is set to the first value.

24. The non-transitory computer-readable medium of claim 19, further comprising instructions that cause the processor to:
determine at least a third threshold based on a multiple of an amplitude of a previous R-wave, wherein the instructions to determine whether the detection of the asystole or the bradycardia is false comprise instructions that cause the processor to:
determine whether the amplitude of the R-wave is below the at least second threshold;
increment a counter value if the amplitude of the R-wave is below the second threshold and decrement the counter value if the amplitude of the R-wave is above the second threshold;
set a flag value to a first value if the amplitude of the R-wave is greater than the at least third threshold and to a second value if the amplitude of the R-wave is less than the at least third threshold; and
determine that the detection of the asystole or the bradycardia is false if the counter value is above a threshold counter value or if the flag value is set to the first value.

* * * * *